United States Patent
Høeg-Jensen et al.

(10) Patent No.: US 9,260,501 B2
(45) Date of Patent: Feb. 16, 2016

(54) PEPTIDE EXTENDED INSULINS

(75) Inventors: Thomas Høeg-Jensen, Klampenborg (DK); Thomas Børglum Kjeldsen, Virum (DK); Jan Markussen, Herlev (DK)

(73) Assignee: Novo Nordisk A/S, Barsvaerd (DK)

( * ) Notice: Subject to any disclaimer, the term of this patent is extended or adjusted under 35 U.S.C. 154(b) by 873 days.

(21) Appl. No.: 12/312,132

(22) PCT Filed: Oct. 29, 2007

(86) PCT No.: PCT/EP2007/061621
§ 371 (c)(1),
(2), (4) Date: Aug. 19, 2009

(87) PCT Pub. No.: WO2008/049931
PCT Pub. Date: May 2, 2008

(65) Prior Publication Data
US 2010/0069605 A1    Mar. 18, 2010

Related U.S. Application Data

(60) Provisional application No. 60/855,191, filed on Oct. 30, 2006.

(30) Foreign Application Priority Data

Oct. 27, 2006 (EP) .................................. 06123103

(51) Int. Cl.
  *A61K 38/28* (2006.01)
  *C07K 14/62* (2006.01)
  *A61K 47/48* (2006.01)

(52) U.S. Cl.
  CPC ........... *C07K 14/62* (2013.01); *A61K 47/48246* (2013.01)

(58) Field of Classification Search
  CPC .......................... C07K 14/62; A61K 47/48246
  USPC ....................................................... 514/5.9
  See application file for complete search history.

(56) References Cited

U.S. PATENT DOCUMENTS

| | | | |
|---|---|---|---|
| 5,618,913 A | 4/1997 | Brange et al. | |
| 5,750,497 A | 5/1998 | Havelund et al. | |
| 6,011,007 A | 1/2000 | Havelund et al. | |
| 6,309,633 B1 | 10/2001 | Ekwuribe et al. | |
| 6,521,738 B2 * | 2/2003 | Kjeldsen et al. | 530/303 |
| 2003/0050228 A1 | 3/2003 | Ekwuribe et al. | |
| 2003/0087808 A1 | 5/2003 | Soltero et al. | |
| 2003/0229010 A1 | 12/2003 | Ekwuribe | |
| 2004/0019000 A1 | 1/2004 | Manoharan et al. | |
| 2004/0022784 A1 * | 2/2004 | Nilsson | 424/140.1 |
| 2004/0038867 A1 | 2/2004 | Still et al. | |
| 2005/0281781 A1 | 12/2005 | Ostroff | |
| 2006/0019872 A1 | 1/2006 | Hong et al. | |
| 2006/0264606 A1 * | 11/2006 | Kjeldsen et al. | 530/303 |

FOREIGN PATENT DOCUMENTS

| | | |
|---|---|---|
| DK | 257197 | 6/1988 |
| DK | 286509 | 1/1999 |
| EP | 254516 | 1/1988 |
| EP | 280534 | 8/1988 |
| JP | 5495785 B2 | 5/2014 |
| WO | WO 01/49870 | 7/2001 |
| WO | WO 03/066859 | 8/2003 |
| WO | 2006/014673 A2 | 2/2006 |
| WO | 2007/007345 A1 | 1/2007 |
| WO | 2007/043059 A1 | 4/2007 |

OTHER PUBLICATIONS

Chu et al., J. Protein Chem. 11: 571-577, 1992.*
Ohnishi et al., J. Am. Chem. Soc. 2006, 128:16338-16344.*
Bevivino et al., PNAS 98: 11955-11960, 2001.*
English Language Abstract of DD257197, published Jun. 8, 1988.
English Language Abstract of DD286509, published Jan. 31, 1999.

* cited by examiner

*Primary Examiner* — Gyan Chandra
(74) *Attorney, Agent, or Firm* — Rosemarie R. Wilk-Orescan

(57) ABSTRACT

Insulins to which there is connected an amino acid oligomer have satisfactory properties.

15 Claims, 1 Drawing Sheet
(1 of 1 Drawing Sheet(s) Filed in Color)

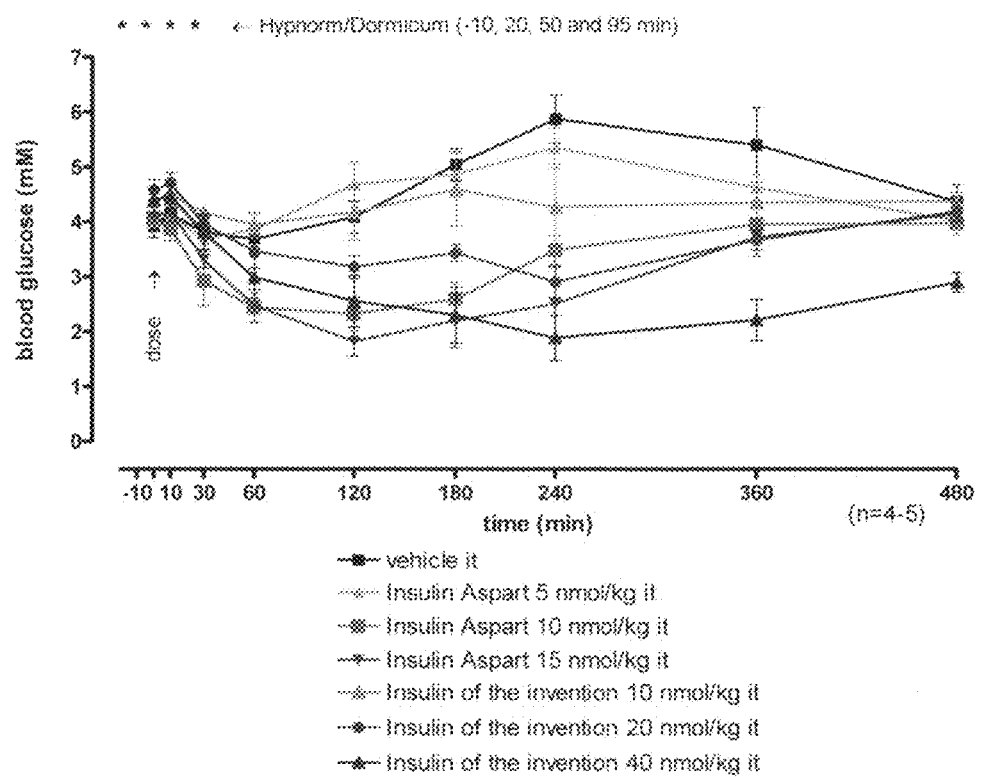

PEPTIDE EXTENDED INSULINS

CROSS-REFERENCE TO RELATED APPLICATIONS

This application is a 35 U.S.C. §371 national stage application of International Patent Application PCT/EP2007/061621 (published as WO 2008/049931), filed Oct. 29, 2007, which claimed priority of European Patent Application 06123103.1, filed Oct. 27, 2006; this application further claims priority under 35 U.S.C. §119 of U.S. Provisional Application 60/855,191, filed Oct. 30, 2006.

FIELD OF THIS INVENTION

The present invention relates to insulins to which there is connected an amino acid oligomer.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Apr. 21, 2009. The Sequence Listing is made up of 4 kilobytes, and the information contained in the attached "SEQUENCE LISTING" is identical to the information in the specification as originally filed. No new matter is added.

BACKGROUND OF THIS INVENTION

Many peptides and proteins are attractive as drug candidates, due to their high bioactivities and receptor selectivities. Peptide and protein drugs are usually administered by injections and this can lead to low patient compliance. Alternative routes of delivery are therefore in demand. Delivery by the pulmonary or oral routes is possible, but usually complicated by low bioavailability due to high proteolytic activity in the relevant organs, and due to low absorption through the relevant tissue. Furthermore, in the human body, peptide and protein drugs are often eliminated quickly from the circulation by proteolytic activity or by elimination via the kidney or liver. It is, therefore, generally desired or necessary to manipulate the drug by formulation or derivatization in order to achieve suitable in vivo half-life.

The object of this invention is to overcome or ameliorate at least one of the disadvantages of the prior art, or to provide a useful alternative.

An aspect of this invention is to improve the absorption of insulins through human tissues.

Another aspect of this invention is to improve the in vivo half-life of insulins.

Another aspect of this invention is to find insulins having a satisfactory physical stability.

Another aspect of this invention is to find insulins having a satisfactory chemical stability.

Another aspect of this invention is to find insulins having a satisfactory proteolytic stability.

Another aspect of this invention is to find insulins having a satisfactory solubility.

DEFINITIONS

Herein, the term "insulin" covers insulin from any species such as porcine insulin, bovine insulin, and human insulin and complexes thereof such as zinc complexes including dimers and oligomers, for example, hexamers thereof. Additionally, the term "insulin" herein covers so-called "insulin analogues". An insulin analogue is an insulin molecule having one or more mutations, substitutions, deletions and/or additions of the A and/or B amino acid chains relative to the native human insulin molecule. More specifically, one or more of the amino acid residues may have been exchanged with another amino acid residue and/or one or more amino acid residue may have been deleted and/or one or two amino acid residue may have been added, with the proviso that said insulin analogue has a sufficient insulin activity. The insulin analogues are preferably such wherein one or more of the naturally occurring amino acid residues, preferably one, two, or three of them, have been substituted by another codable amino acid residue. Thus position 28 of the B chain may be modified from the natural Pro residue to one of Asp, Lys or Ile. In another embodiment, Lys at position B29 is modified to Pro; also, Asn at position A21 may be modified to Ala, Gln, Glu, Gly, His, Ile, Leu, Met, Ser, Thr, Trp, Tyr or Val, in particular to Gly, Ala, Ser or Thr and, preferably, to Gly. Furthermore, Asn at position B3 may be modified to Lys. Further examples of insulin analogues are desB30 human insulin and desB1 human insulin. Examples of insulin analogues are described in the following patents and equivalents thereto: U.S. Pat. No. 5,618,913, EP 254,516, EP 280,534, U.S. Pat. No. 5,750,497 and U.S. Pat. No. 6,011,007. Examples of specific insulin analogues are insulin aspart (i.e., Asp$^{B28}$ human insulin) and insulin lispro (i.e., Lys$^{B28}$,Pro$^{B29}$ human insulin). In one aspect of this invention, the term insulin analogues does not cover insulin molecules having additions of the A and/or B chain meaning the A chain consists of not more than 21 amino acid residues and the B chain consists of not more than 30 amino acid residues. In another aspect of this invention, the term insulin analogues does not cover insulin molecules wherein more than 6 amino acid residues, preferably not more than 4 amino acid residues, and even more preferred preferably not more than 2 amino acid residues, have been exchanged, compared with human insulin. In another aspect of this invention, the term insulin analogues does not cover insulin molecules wherein more than 2 amino acid residues, preferably not more than 1 amino acid residues, have or has been deleted, compared with human insulin.

Herein, the term "an insulin residue" covers insulin, as defined above, from which a hydrogen atom has been removed from an amino group and/or a hydroxy group has been removed from a carboxy group.

Herein, the known and generally used 1 or 3 letter codes have been used for the amino acids.

The term "amino acid residue" covers an amino acid from which a hydrogen atom has been removed from the amino group and/or a hydroxy group has been removed from the carboxy group.

Herein, the amino acids are, preferably, codable (alpha) amino acids.

The term "oligomer" herein covers repeating units of monomers (amino acid residues). The number of monomers in the oligomers can be as many as 800.

The term "amino acid oligomer" herein covers a chain of amino acids, preferably codable (alpha) amino acids, of rather uniform sequence. Examples of such amino acid oligomers are homo-oligomers of e.g. glycine, or repeating units of di- or tri-peptides.

The term "amino acid oligomer residue" herein covers an amino acid oligomer from which a hydrogen atom has been removed from the amino group and/or a hydroxy group has been removed from the carboxy group, i.e. a monomer of the oligomer.

The term "codable amino acid" herein covers an amino acid which can be coded for by a triplet ("codon") of nucleotides.

In vivo, human insulin is synthesized as a so called single-chain precursor proinsulin (preproinsulin) consisting of a prepeptide having 24 amino acid followed by proinsulin containing 86 amino acids in the following configuration: prepeptide-B-Arg-Arg-C-Lys-Arg-A, in which A and B are the A and B chains of insulin, respectively, C is the so-called connecting peptide having 31 amino acids and wherein there are the 3 disulfide bridges between the Cys residues. Herein, the term single chain insulin covers the molecule prepeptide-B-Arg-Arg-C-Lys-Arg-A, wherein the A and B chains corresponds to the A and B chains, respectively, of the insulin analogue in question. Herein, said connecting peptide may also be designated the C peptide.

The term "treatment" as used herein means the prevention, management and care of a patient for the purpose of combating a disease, disorder or condition. The term is intended to include the prevention of the disease, delaying of the progression of the disease, disorder or condition, the alleviation or relief of symptoms and complications, and/or the cure or elimination of the disease, disorder or condition. The patient to be treated is preferably a mammal, in particular a human being.

The term "hydrophobicity" herein is used as hydrophobicity relative to human insulin and is measured by HPLC as described for "assay V".

SUMMARY OF THE INVENTION

This invention relates to insulins to which one or more amino acid oligomer(s) is/are attached and, herein, such products are designated extended insulins. Thereby, the biophysical properties of the extended insulin such as polarity, solubility and size are modulated. The biophysical properties of the extended insulin can be fine-tuned by varying the type of amino acid in the attached oligomer as well as the length of the oligomer. These altered biophysical properties of the extended insulins of the invention result in prolonged action profile following administration to the patient and of products being suitable for oral or pulmonary administration.

The patent or application file contains at least one drawing executed in color. Copies of this patent or patent application publication with color drawing(s) will be provided by the Office upon request and payment of the necessary fee.

BRIEF DESCRIPTION OF THE DRAWING

FIG. 1 shows the effects of various insulins on blood glucose levels in rats after intratracheal drop administration.

DESCRIPTION OF THE PREFERRED EMBODIMENTS

It has, unexpectedly, been found that long extensions by amino acid oligomers of the C-terminal ends of the A- or B-chains of insulins (and N-terminal end of the B-chain)— extended insulins of this invention—have interesting properties: a) They possess largely preserved insulin receptor affinities, and b) they show prolonged action profiles following in vivo administration.

Formally, the extended insulins of this invention are build from an insulin as defined above and one or more amino acid oligomer(s). In the extended insulins of this invention, one end of the amino acid oligomer is attached to the insulin residue via a peptide bond but the other end of said amino acid oligomer is not attached to the insulin residue.

The amino acid oligomer can, for example, be attached to the insulin residue by recombinant methods. Such methods are known per se and they are, for example, described below.

The extended insulins of the invention can, for example, be produced by expressing a DNA sequence encoding the extended insulin of the invention in question in a suitable host cell by well known technique as disclosed in e.g. U.S. Pat. No. 6,500,645. The extended insulin of the invention is either expressed directly as a single chain insulin comprising a C-peptide or a peptide bond connecting the B-chain C-terminal to the A-chain N-terminal or as a precursor molecule also comprising a single chain insulin but also containing an N-terminal precursor extension on the B-chain. This N-terminal precursor extension may have the function of increasing the yield of the directly expressed product and may be of up to 15 amino acid residues long. The N-terminal precursor extension is to be cleaved of in vitro after isolation from the culture broth and will therefore have a cleavage site (Lys or Arg) next to the B-chain N-terminal. N-terminal precursor extensions of the type suitable in the present invention are disclosed in U.S. Pat. No. 5,395,922 and European Patent No. 765,395A. An example of such a precursor extension is EEAEAEAPK. This precursor extension is cleaved off from the precursor single chain insulin by proteolysis, eg, by trypsin or trypsin-like proteases. This cleavage also cleaves off the C-peptide (or, if there is no C peptide, cleaves the bond between the N terminal end of the A chain (e.g., A1) and the C terminal end of the B chain (e.g. B30)) and thus converts the precursor single chain insulin to matured two-chain insulin molecules. The extended insulins of the invention do not contain such precursor extensions and the extended insulins of the invention are all matured two-chain insulin molecules.

The polynucleotide sequence coding for the respective extended insulin polypeptide may be prepared synthetically by established standard methods, e.g. the phosphoamidite method described by Beaucage et al. (1981) Tetrahedron Letters 22:1859-1869, or the method described by Matthes et al. (1984) EMBO Journal 3:801-805. According to the phosphoamidite method, oligonucleotides are synthesized, for example, in an automatic DNA synthesizer, purified, duplexed and ligated to form the synthetic DNA construct. A currently preferred way of preparing the DNA construct is by polymerase chain reaction (PCR).

The polynucleotide sequences may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The recombinant vector capable of replicating in the selected microorganism or host cell and which carries a polynucleotide sequence encoding the extended insulin polypeptide in question may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated.

Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

In one embodiment, the recombinant expression vector is capable of replicating in yeast. Examples of sequences which enable the vector to replicate in yeast are the yeast plasmid 2 µm replication genes REP 1-3 and origin of replication.

The vectors may contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyltransferase), pyrG (orotidine-5'-phosphate decarboxylase) and trpC (anthranilate synthase. Suitable markers for yeast host cells are ADE2, HIS3, LEU2, LYS2, MET3, TRP1, and URA3. A well suited selectable marker for yeast is the *Schizosaccharomyces pompe* TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Ma1, TPI, ADH or PGK promoters.

The polynucleotide construct will also typically be operably connected to a suitable terminator. In yeast a suitable terminator is the TPI terminator (Alber et al. (1982) J. Mol. Appl. Genet. 1:419-434).

The procedures used to ligate the individual polynucleotide sequences contained in the expression vector such as DNA coding for the desired insulin polypeptide, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the single-chain insulins of the invention, and subsequently inserting this fragment into a suitable expression vector, or by sequentially inserting DNA fragments containing genetic information for the individual elements (such as the signal, pro-peptide, connecting peptide, A and B chains) followed by ligation.

The vector comprising such polynucleotide sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, *Streptomyces* cell, or gram negative bacteria such as *E. coli* and *Pseudomonas* sp. Eukaryote cells may be mammalian, insect, plant, or fungal cells. In a preferred embodiment, the host cell is a yeast cell. The yeast organism used in the process of the invention may be any suitable yeast organism which, on cultivation, produces large amounts of the single chain insulin of the invention. Examples of suitable yeast organisms are strains selected from the yeast species *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*.

The transformation of the yeast cells may for instance be effected by protoplast formation followed by transformation in a manner known per se. The medium used to cultivate the cells may be any conventional medium suitable for growing yeast organisms. The secreted insulin polypeptide, a significant proportion of which will be present in the medium in correctly processed form, may be recovered from the medium by conventional procedures including separating the yeast cells from the medium by centrifugation, filtration or catching the insulin precursor by an ion exchange matrix or by a reverse phase absorption matrix, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

In an embodiment, the in vivo half life of certain extended insulins of this invention is improved, making them suitable for once weekly administration.

In an embodiment, the in vivo half life of certain extended insulins of this invention is improved, making them suitable for bi-daily administration.

In an embodiment, the in vivo half life of certain extended insulins of this invention is improved, making them suitable for once daily administration.

In an embodiment, the in vivo half life of certain extended insulins of this invention is improved, making them suitable for twice daily administration.

In an embodiment, the in vivo half life of certain extended insulins of this invention is improved, making them suitable for thrice daily administration.

In another embodiment, the hydrophobicity of the extended insulins of the invention is <25.

In another embodiment, the hydrophobicity of the extended insulins of the invention is <20.

In another embodiment, the hydrophobicity of the extended insulins of the invention is <15.

In another embodiment, the hydrophobicity of the extended insulins of the invention is <10.

In another embodiment, the hydrophobicity of the extended insulins of the invention is <5.

In another embodiment, the hydrophobicity of the extended insulins of the invention is <1.

In another embodiment, the hydrophobicity of the extended insulins of the invention is <0.5.

In another embodiment, the hydrophobicity of the extended insulins of the invention is <0.1.

In another embodiment, the hydrophobicity of the extended insulins of the invention is <0.05.

In another embodiment, the hydrophobicity of the extended insulins of the invention is <0.01.

Pharmaceutical Administration

The compound of this invention, i.e., the extended insulin, can, for example, be administered subcutaneously, orally, or pulmonary.

For subcutaneous administration, an extended insulin of this invention is formulated analogously with the formulation of known insulins. Furthermore, for subcutaneous administration, an extended insulin of this invention is administered analogously with the administration of known insulins and, generally, the physicians are familiar with this procedure.

For oral administration, an extended insulin of this invention is formulated analogously with the formulation of other medicaments which are to be administered orally. Furthermore, for oral administration, an extended insulin of this invention is administered analogously with the administration of known oral medicaments and, principally, the physicians are familiar with such procedure.

For pulmonary products, the following details are given: The extended insulin of this invention may be administered by inhalation in a dose effective manner to increase circulating insulin levels and/or to lower circulating glucose levels. Such administration can be effective for treating disorders such as diabetes or hyperglycemia. Achieving effective doses of insulin requires administration of an inhaled dose of more than about 0.5 µg/kg to about 50 µg/kg of an extended insulin of this invention. A therapeutically effective amount can be determined by a knowledgeable practitioner, who will take into account factors including insulin level, blood glucose levels, the physical condition of the patient, the patient's pulmonary status, or the like.

According to the invention, an extended insulin of this invention may be delivered by inhalation to achieve absorption thereof. Administration by inhalation can result in pharmacokinetics comparable to subcutaneous administration of insulins. Inhalation of an extended insulin of this invention leads to a rise in the level of circulating insulin followed by a fall in blood glucose levels. Different inhalation devices typically provide similar pharmacokinetics when similar particle sizes and similar levels of lung deposition are compared.

According to the invention, an extended insulin of this invention may be delivered by any of a variety of inhalation devices known in the art for administration of a therapeutic agent by inhalation. These devices include metered dose inhalers, nebulizers, dry powder generators, sprayers, and the like. Preferably, an extended insulin of this invention is delivered by a dry powder inhaler or a sprayer. There are several desirable features of an inhalation device for administering an extended insulin of this invention. For example, delivery by the inhalation device is advantageously reliable, reproducible, and accurate. The inhalation device should deliver small particles, for example, less than about 10 µm, for example about 1-5 µm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of an extended insulin of this invention, the quantity of the formulation delivered, and the duration of administration of a single dose depend on the type of inhalation device employed. For some aerosol delivery systems, such as nebulizers, the frequency of administration and length of time for which the system is activated will depend mainly on the concentration of an extended insulin of this invention in the aerosol. For example, shorter periods of administration can be used at higher concentrations of an extended insulin of this invention in the nebulizer solution. Devices such as metered dose inhalers can produce higher aerosol concentrations, and can be operated for shorter periods to deliver the desired amount of an extended insulin of this invention. Devices such as powder inhalers deliver active agent until a given charge of agent is expelled from the device. In this type of inhaler, the amount of an extended insulin of this invention in a given quantity of the powder determines the dose delivered in a single administration.

The particle size of an extended insulin of this invention in the formulation delivered by the inhalation device is critical with respect to the ability of insulin to make it into the lungs, and preferably into the lower airways or alveoli. Preferably, the extended insulin of this invention is formulated so that at least about 10% of the insulin of this invention delivered is deposited in the lung, preferably about 10 to about 20%, or more. It is known that the maximum efficiency of pulmonary deposition for mouth breathing humans is obtained with particle sizes of about 2 µm to about 3 µm. When particle sizes are above about 5 mµ, pulmonary deposition decreases substantially. Particle sizes below about 1 µm cause pulmonary deposition to decrease, and it becomes difficult to deliver particles with sufficient mass to be therapeutically effective. Thus, particles of an extended insulin of this invention delivered by inhalation have a particle size preferably less than about 10 µm, more preferably in the range of about 1 µm to about 5 µm. The formulation of an extended insulin of this invention is selected to yield the desired particle size in the chosen inhalation device.

Advantageously for administration as a dry powder, compounds of this invention is prepared in a particulate form with a particle size of less than about 10 µm, preferably about 1 to about 5 µm. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 µm. Such formulations can be achieved by spray drying, milling, or critical point condensation of a solution containing an extended insulin of this invention and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. One suitable dry powder inhaler is the Turbohaler™ manufactured by Astra (Sødertalje, Sweden). In another type of inhaler, air flow generated by the patient's inhalation activates an impeller motor which deagglomerates the monomeric insulin analogue particles. The Dura Spiros™ inhaler is such a device.

Formulations of an extended insulin of this invention for administration from a dry powder inhaler typically include a finely divided dry powder containing an extended insulin of this invention, but the powder can also include a bulking agent, carrier, excipient, another additive, or the like. Additives can be included in a dry powder formulation of an extended insulin of this invention, for example, to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The insulin of this invention can be mixed with an additive at a molecular level or the solid formulation can include particles of an extended insulin of this invention mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including an extended insulin of this invention can be produced by forcing a suspension or solution of an extended insulin of this invention through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of an extended insulin of this invention delivered by a sprayer have a particle size less than about 10 µm, preferably in the range of about 1 µm to about 5 µm.

Formulations of an extended insulin of this invention suitable for use with a sprayer typically include an extended insulin of this invention in an aqueous solution at a concentration of about 1 mg to about 20 mg of an extended insulin of this invention per ml of solution. The formulation can include agents such as an excipient, a buffer, an isotonicity agent, a preservative, a surfactant, and, preferably, zinc. The formulation can also include an excipient or agent for stabilization of the insulin of this invention, such as a buffer, a reducing agent, a bulk protein, or a carbohydrate. Bulk proteins useful in formulating insulins of this invention include albumin, protamine, or the like. Typical carbohydrates useful in formulating insulins of this invention include sucrose, mannitol, lactose, trehalose, glucose, or the like. The insulin of this invention formulation can also include a surfactant, which can reduce or prevent surface-induced aggregation of the insulin of this invention caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation. Especially preferred surfactants for purposes of this invention are polyoxyethylene sorbitan monooleate, polysorbate 80, polysorbate 20, or the like. Additional agents known in the art for formulation of a protein such as insulin analogue protein can also be included in the formulation.

An extended insulin of this invention can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of an extended insulin of this invention through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of insulin of this invention either directly or through a coupling fluid, creating an aerosol including the insulin of this invention. Advantageously, particles of an extended insulin of this invention delivered by a nebulizer have a particle size less than about 10 µm, preferably in the range of about 1 µm to about 5 µm.

Formulations of an extended insulin of this invention suitable for use with a nebulizer, either jet or ultrasonic, typically include an extended insulin of this invention in an aqueous solution at a concentration of about 1 mg to about 20 mg of an extended insulin of this invention per ml of solution. The formulation can include agents such as an excipient, a buffer, an isotonicity agent, a preservative, a surfactant, and, preferably, zinc. The formulation can also include an excipient or agent for stabilization of the insulin of this invention, such as a buffer, a reducing agent, a bulk protein, or a carbohydrate. Bulk proteins useful in formulating insulins of this invention include albumin, protamine, or the like. Typical carbohydrates useful in formulating insulins of this invention include sucrose, mannitol, lactose, trehalose, glucose, or the like. The extended insulin of this invention formulation can also include a surfactant, which can reduce or prevent surface-induced aggregation of the extended insulin of this invention caused by atomization of the solution in forming an aerosol. Various conventional surfactants can be employed, such as polyoxyethylene fatty acid esters and alcohols, and polyoxyethylene sorbital fatty acid esters. Amounts will generally range between about 0.001 and about 4% by weight of the formulation. Especially preferred surfactants for purposes of this invention are polyoxyethylene sorbitan monooleate, polysorbate 80, polysorbate 20, or the like. Additional agents known in the art for formulation of a protein such as insulin analogue protein can also be included in the formulation.

In a metered dose inhaler (MDI), a propellant, an extended insulin of this invention, and any excipients or other additives are contained in a canister as a mixture including a liquefied compressed gas. Actuation of the metering valve releases the mixture as an aerosol, preferably containing particles in the size range of less than about 10 µm, preferably about 1 µm to about 5 µm. The desired aerosol particle size can be obtained by employing a formulation of an extended insulin of this invention produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of an extended insulin of this invention for use with a metered-dose inhaler device will generally include a finely divided powder containing an extended insulin of this invention as a suspension in a non aqueous medium, for example, suspended in a propellant with the aid of a surfactant. The propellant may be any conventional material employed for this purpose, such as chloro-fluorocarbon, a hydrochlorofluorocarbon, a hydrofluorocarbon, or a hydrocarbon, including trichloro-fluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. The surfactant can be chosen to stabilize the extended insulin of this invention as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as insulin analogue protein can also be included in the formulation.

One of ordinary skill in the art will recognize that the methods of the current invention may be achieved by pulmonary administration of an extended insulin of this invention via devices not described herein.

The present invention also relates to a pharmaceutical composition or formulation including an extended insulin of this invention and suitable for administration by inhalation. According to the invention, an extended insulin of this invention can be used for manufacturing a formulation or medicament suitable for administration by inhalation. The invention also relates to methods for manufacturing formulations including an extended insulin of this invention in a form that is suitable for administration by inhalation. For example, a dry powder formulation can be manufactured in several ways, using conventional techniques. Particles in the size range appropriate for maximal deposition in the lower respiratory tract can be made by micronizing, milling, spray drying, or the like. And a liquid formulation can be manufactured by dissolving an extended insulin of this invention in a suitable solvent, such as water, at an appropriate pH, including buffers or other excipients.

Hence, in an embodiment, this invention relates to a method of administering an extended insulin of this invention comprising administering an effective amount of said compound to a patient in need thereof by pulmonary means; and, preferably, said compound is inhaled through the mouth of said patient.

Another object of the present invention is to provide a pharmaceutical formulation comprising an extended insulin according to the present invention which is present in a concentration from 0.1 mg/ml to 500 mg/ml, and wherein said formulation has a pH from 2.0 to 10.0. The formulation may further comprise protease inhibitor(s), a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% (weight/weight) water. Likewise, the term "aqueous solution" is defined as a solution comprising at least 50% (weight/weight) water, and the term "aqueous suspension" is defined as a suspension comprising at least 50% (weight/weight) water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of an extended insulin of the present invention, and a buffer, wherein said extended insulin is present in a concentration from 0.1 mg/ml or above, and wherein said formulation has a pH from about 2.0 to about 10.0.

Formulations intended for oral use may be prepared according to any known method, and such formulations may contain one or more agents selected from the group consisting of sweetening agents, flavouring agents, colouring agents, and preserving agents in order to provide pharmaceutically elegant and palatable preparations. Tablets may contain the active ingredient in a mixture with non-toxic pharmaceutically-acceptable excipients which are suitable for the manufacture of tablets. These excipients may be for example, inert diluents, such as mannitol, maltodextrin, kaolin, calcium carbonate, sodium carbonate, lactose, calcium phosphate or sodium phosphate; granulating and disintegrating agents, for example corn starch; binding agents, for example, starch, gelatine, polymers or acacia; and lubricating agents, for example magnesium stearate, stearic acid or talc. The tablets may be uncoated or they may be coated by known techniques to delay disintegration or release of the therapeutically active polypeptide.

The orally administerable formulations of the present invention may be prepared and administered according to methods well known in pharmaceutical chemistry, see Remington's Pharmaceutical Sciences, $17^{th}$ ed. (A. Osol ed., 1985).

In one aspect of the invention, the pharmaceutical compositions of the present invention may be administered by means of solid dosage forms such as tablets and capsules. The tablets may be prepared by wet granulation, by dry granulation, by direct compression or melt granulation.

Tablets for this invention may be prepared utilizing conventional tabletting techniques. A general method of manufacture involves blending of an extended insulin, a water-soluble diluent, hydrophilic binder and optionally a portion of a disintegrant. This blend is then granulated with an aqueous solution of the hydrophilic binder or an aqueous solution of the hydrophilic binder and surfactant and milled, if necessary. The granules are dried and reduced to a suitable size. Any other ingredients, such as lubricants, (e.g. magnesium stearate) and additional disintegrants, are added to the granules and mixed. This mixture is then compressed into a suitable size and shape using conventional tabletting machines such as a rotary tablet press. The tablets may be film coated by techniques well known in the art.

Formulations for oral use may also be presented as hard or soft gelatine capsules where the active ingredient is mixed with an inert solid diluent, for example, such as mannitol, maltodextrin, calcium carbonate, sodium carbonate, lactose, kaolin, calcium phosphate or sodium phosphate, or a soft gelatine capsule wherein the active ingredient is mixed with water or an oil medium, for example peanut oil, liquid paraffin, or olive oil.

Capsules for this invention may be prepared utilizing conventional methods. A general method of manufacture involves blending a therapeutically active peptide, alginate, a water-soluble diluent, a hydrophilic binder, and optionally a portion of a disintegrant. This blend is then granulated with an aqueous solution of the hydrophilic binder or an aqueous solution of the hydrophilic binder and surfactant in water, and milled, if necessary. The granules are dried and reduced to a suitable size. Any other ingredients, such as a lubricant, are added to the granules and mixed. The resulting mixture is then filled into a suitable size hard-shell gelatin capsule using conventional capsule-filling machines.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. The preservative is present in an amount sufficient to obtain a preserving effect. The amount of preservative in a pharmaceutical formulation is the well-known to the skilled person and may be determined from e.g. literature in the field and/or the known amount(s) of preservative in e.g. commercial products. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabilizer. The term "stabiliser" as used herein refers to chemicals added to polypeptide containing pharmaceutical formulations in order to stabilize the peptide, i.e. to increase the shelf life and/or in-use time of such formulations. The use of a stabilizer in pharmaceutical compositions is well-known to the skilled person. For convenience reference is made to Remington: *The Science and Practice of Pharmacy*, 19$^{th}$ edition, 1995.

In a further embodiment of the invention the formulation further comprises a surfactant. The term "surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "Detergent" is a synonym used for surfactants in general. The use of a surfactant in pharmaceutical compositions is well-known to the skilled person. For convenience reference is made to Remington: *The Science and Practice of Pharmacy*, 19$^{th}$ edition, 1995.

In a further embodiment of the invention the formulation further comprises protease inhibitors.

It is possible that other ingredients may be present in the extended insulin pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

To be more precise, this invention also relates to the following embodiments:

a) The method as described herein, wherein the extended insulin of this invention is delivered to the lower airways of the patient.

b) The method as described herein, wherein the extended insulin of this invention is deposited in the alveoli.

c) The method as described herein, wherein the extended insulin of this invention is administered as a pharmaceutical formulation comprising the extended insulin of this invention in a pharmaceutically acceptable carrier.

d) The method as described herein, wherein the formulation is selected from the group consisting of a solution in an aqueous medium and a suspension in a non-aqueous medium.

e) The method as described herein, wherein the formulation is administered as an aerosol.

f) The method as described herein, wherein the formulation is in the form of a dry powder.

g) The method as described herein, wherein the formulation has a particle size of less than about 10 microns.

h) The method as described herein, wherein the formulation has a particle size of about 1 to about 5 microns.

i) The method as described herein, wherein the formulation has a particle size of about 2 to about 3 microns.

j) The method as described herein, wherein at least about 10% of the extended insulin of this invention delivered is deposited in the lung.

k) The method as described herein, wherein the extended insulin of this invention is delivered from an inhalation device suitable for pulmonary administration and capable of depositing the insulin analog in the lungs of the patient.

l) The method as described herein, wherein the device is selected from the group consisting of a nebulizer, a metered-dose inhaler, a dry powder inhaler, and a sprayer.

m) The method as described herein, wherein the device is a dry powder inhaler.

n) The method as described herein, wherein the device is a nebulizer.

o) The method as described herein, wherein the device is a metered-dose inhaler.

p) The method as described herein, wherein the device is a sprayer.

q) The method as described herein, wherein actuation of the device administers from about 3 µg/kg to about 20 µg/kg of an extended insulin of this invention, preferably from about 7 µg/kg to about 14 µg/kg of an extended insulin of this invention.

r) The method as described herein, wherein said extended insulin of this invention is any of the compounds mentioned specifically in any of the examples herein.

s) A method as described herein for treating diabetes comprising administering an effective dose of an extended insulin of this invention to a patient in need thereof by pulmonary means.

t) The method as described herein, wherein the extended insulin of this invention is any of the specific extended insulin of this invention specifically mentioned herein, especially in the specific examples herein.

Even though the above embodiments are here described specifically in relation a method, they apply analogously for the product or formulation to be used.

Preferred Features of this Invention

To sum up, the features of this invention are as follows:

1. An extended insulin being an insulin residue (as defined above) attached to one or more amino acid oligomer residues containing at least 5 amino acid residues, preferably at least 10 amino acid residues, more preferred at least 15 amino acid residues, and not more than 800 amino acid residues, preferably not more than 300 amino acid residues, preferably not more than 100 amino acid residues, preferably not more than 50 amino acid residues, by an amide bond, preferably by a peptide bond.
2. The extended insulin of the preceding clause, wherein the amino acid oligomer residue is composed of the codable amino acid residues.
3. The extended insulin of the preceding clause, wherein the amino acid oligomer residue does not contain a lysine residue.
4. The extended insulin of any of the preceding, possible clauses, wherein the amino acid oligomer residue is composed of amino acid residues elected among the group consisting of Gly, Glu, Pro and Ser residues. These amino acid residues may be the same or different and may be arranged in any order.
5. The extended insulin of the preceding clause, wherein the amino acid oligomer residue is composed of Gly residues.
6. The extended insulin of any of the preceding, possible clauses, wherein the amount of Gly residues in the amino acid oligomer residue is at least 80% (weight/weight).
7. The extended insulin of any of the preceding, possible clauses, wherein the amount of Gly residues in the amino acid oligomer residue is at least 80% (by numbers).
8. The extended insulin of any of the preceding, possible clauses, wherein the amount of Gly residues in the amino acid oligomer is at least 85% (by numbers).
9. The extended insulin of any of the preceding, possible clauses, wherein the amount of Gly residues in the amino acid oligomer residue is at least 90% (by numbers).
10. The extended insulin of any of the preceding, possible clauses, wherein the amount of Gly residues in the amino acid oligomer residue is at least 95% (by numbers).
11. The extended insulin of any of the preceding, possible clauses, wherein the amino acid oligomer residue is $(Gly)_n$, $(Gly-Pro-Pro)_n$, $(Pro-Pro-Gly)_n$, $(Gly-Ser)_n$, $(Ser-Gly)_n$, $(Gly-Glu)_n$ or $(Glu-Gly)_n$, wherein n is an integer giving the proper number of amino acid residues.
12. The extended insulin of any of the preceding, possible clauses, wherein the amino acid oligomer residue is attached to an amino acid residue in one of the positions B1, A21, B29 or B30 of insulin, provided said amino acid is in a terminal position prior to attachment of the oligomer residue. If the amino acid in said B1, A21, B29 or B30 position is not in a terminal position, the amino acid oligomer residue is attached to an amino acid residue in one of the positions B0, B(−1), A22, A23, B31 or B32 of insulin.
13. The extended insulin of any of the preceding, possible clauses, wherein any oligomer attached to the C terminal end of the B chain is terminated by an arginine residue.
14. The extended insulin of any of the preceding, possible clauses, wherein the amino acid oligomer residue is attached to an amino acid residue in one of the positions B29 or B30 of insulin, provided said amino acid is in a terminal position prior to attachment of the oligomer and wherein the said oligomer is terminated by an arginine residue.
15. The extended insulin of any of the preceding, possible clauses, wherein the insulin residue contains not more than 51 amino acid residues.
16. The extended insulin of any of the preceding, possible clauses, wherein the insulin residue is human insulin having one or more of the following optional modifications: A14: E or D; A21: G, A or Q; B3: Q, S or T; B25: H; B28: D or E; B30: des (i.e., desB30).
17. The extended insulin of any of the preceding, possible clauses, wherein the insulin residue is a residue of human insulin, desB30 human insulin, insulin aspart, A21 Gly human insulin, A21 Gly desB30 human insulin, Lispro or glulisine.
18. The extended insulin of any of the preceding, possible clauses, wherein there is only attached a single oligomer residue to the insulin residue.
19. The extended insulin of any of the preceding, possible clauses, except the last one, wherein there is attached exactly two oligomer residues to the insulin residue.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (EPO guidelines C 4.13).

This invention includes all modifications and equivalents of the subject matter recited in the claims appended hereto as permitted by applicable law.

The following examples are offered by way of illustration, not by limitation.

General Procedures:

Construction of Expression Vectors, Transformation of the Yeast Cells, and Expression of the Insulin Precursors of the Invention All expressions plasmids are of the C-POT type, similar to those described in EP 171142, which are characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator. These sequences are similar to the corresponding sequences in plasmid pKFN1003 (described in WO 90/10075) as are all sequences except the sequence of the EcoRI-XbaI fragment encoding the fusion protein of the leader and the insulin product. In order to express different fusion proteins, the EcoRI-XbaI fragment of pKFN1003 is simply replaced by an EcoRI-XbaI fragment encoding the leader-insulin fusion of interest. Such EcoRI-XbaI fragments may be synthesized using synthetic oligonucleotides and PCR according to standard techniques.

Yeast transformants were prepared by transformation of the host strain S. cerevisiae strain MT663 (MATa/MATα pep4-3/pep4-3 HIS4/his4 tpi::LEU2/tpi::LEU2 Cir$^+$). The yeast strain MT663 was deposited in the Deutsche Sammlung von Mikroorganismen and Zellkulturen in connection with filing WO 92/11378 and was given the deposit number DSM 6278.

MT663 was grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM Na$_2$EDTA pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM Na$_2$EDTA, 0.1 M sodium citrate, pH 0 5.8, and 2 mg Novozym®234. The suspension was incubated at 30° C. for 30 minutes, the cells collected by centrifugation, washed in 10 ml of 1.2 M sorbitol and 10 ml of CAS (1.2 M sorbitol, 10 mM CaCl$_2$, 10 mM Tris HCl (pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM CaCl$_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM CaCl$_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) Methods in Yeast Genetics, Cold Spring Harbor Laboratory) containing 1.2 M sorbitol plus 2.5% agar) at 52° C. was added and the suspension poured on top of plates containing the same agar-solidified, sorbitol containing medium. S. cerevisiae strain MT663 transformed with expression plasmids was grown in YPD for 72 h at 30° C.

The extended insulin precursors (single chain precursors) have the following extension to the B-chain N-terminal: EEAEAEAPK and contain the following C-peptide: DGK.

The extended insulin precursor was converted into the corresponding two-chain desB30 insulin analogue by Achromobacter lyticus lysine specific protease (ALP) immobilised on Sepharose (EC 3.4.21.50). For each insulin analogue precursor 3 ml yeast culture supernatant was transferred to a new tube and 666 µl of ALP, dissolved in 0.2 M NaHCO$_3$ pH 9.1, was added. The solution had a pH value of about 8.1, which is within the pH optimum range for the enzyme and the mixture was incubated for 1.5 h under gentle agitation.

Production, Purification and Characterization of the Extended Insulins of the Invention A number of insulin precursors were produced as described above and isolated from the culture medium and purified.

These extended insulins were tested for biological insulin activity as measured by binding affinity to the human insulin receptor relative to that of human insulin as described below. It can be an advantage to assess the binding affinities of the insulins prior to purification. This can be done by assaying the culture supernatants.

The extended insulins of this invention can be purified by employing one or more of the following procedures which are typical within the art. These procedures can—if needed—be modified with regard to gradients, pH, salts, concentrations, flow, columns and so forth. Depending on factors such as impurity profile, solubility of the insulins in question etcetera, these modifications can readily be recognised and made by a person skilled in the art.

After acidic HPLC or desalting, the compounds are isolated by lyophilisation of the pure fractions.

After neutral HPLC or anion exchange chromatography, the compounds are desalted, precipitated at isoelectrical pH, or purified by acidic HPLC.

Typical Purification Procedures:

The HPLC system is a Gilson system consisting of the following: Model 215 Liquid handler, Model 322-H2 Pump and a Model 155 UV Dector. Detection is typically at 210 nm and 280 nm.

The Äkta Purifier FPLC system (Amersham Biosciences) consists of the following: Model P-900 Pump, Model UV-900 UV detector, Model pH/C-900 pH and conductivity detector, Model Frac-950 Fraction collector. UV detection is typically at 214 nm, 254 nm and 276 nm.

Acidic HPLC:

| Column: | Macherey-Nagel SP 250/21 Nucleusil 300-7 C4 |
|---|---|
| Flow: | 8 ml/min, |

Buffer A: 0.1% TFA in acetonitrile
Buffer B: 0.1% TFA in water.

| Gradient: | 0.0-5.0 min: | 10% A |
|---|---|---|
| | 5.00-30.0 min: | 10% A to 90% A |
| | 30.0-35.0 min: | 90% A |
| | 35.0-40.0 min: | 100% A |

Neutral HPLC:

| Column: | Phenomenex, Jupiter, C4 5 µm 250 × 10,00 mm, 300 Å |
|---|---|
| Flow: | 6 ml/min |

Buffer A: 5 mM TRIS, 7.5 mM (NH$_4$)$_2$SO$_4$, pH=7.3, 20% CH$_3$CN
Buffer B: 60% CH$_3$CN, 40% water

| Gradient: | 0-5 min: | 10% B, |
|---|---|---|
| | 5-35 min: | 10-60% B |
| | 35-39 min: | 60% B, |
| | 39-40 min: | 70% B |
| | 40-43.5 min: | 70% B |

19

Anion exchange chromatography:

| Column: | RessourceQ, 6 ml |
|---|---|
| Flow: | 6 ml/min |

Buffer A: 0.09% NH$_4$HCO$_3$, 0.25% NH$_4$OAc, 42.5% ethanol pH 8.4
Buffer B: 0.09% NH$_4$HCO$_3$, 2.5% NH$_4$OAc, 42.5% ethanol pH 8.4
Gradient: 100% A to 100% B during 30 column volumes Desalting:

| Column: | HiPrep 26/10 |
|---|---|
| Flow: | 10 ml/min, 6 column volumes |
| Buffer: | 10 mM NH$_4$HCO$_3$ |

The following insulins of the invention have been prepared as described above:

Example 1

A22-27G desB30 Human Insulin

```
                    S————S
                    |    |
H-GIVEQCCTSICSLYQLENYCNGGGGGG-OH
       |                |
       S                S
       |                |
       S                S
       |                |
 H-FVNQHLCGSHLVEALYLVCGERGFFYTPK-OH
```

MALDI-MS (matrix: sinapinic acid); m/z: 6048.8, Calculated: 6050.

20

Example 2

A22-33G desB30 Human Insulin

```
                    S————S
                    |    |
H-GIVEQCCTSICSLYQLENYCNGGGGGGGGGGGG-OH
       |                |
       S                S
       |                |
       S                S
       |                |
 H-FVNQHLCGSHLVEALYLVCGERGFFYTPK-OH
```

DGK-Single-Chain Precursor:
MALDI-MS (matrix: sinapinic acid); m/z: 7628, Calculated: 7629.

Example 3

A22-39G desB30 Human Insulin

```
                    S————S
                    |    |
H-GIVEQCCTSICSLYQLENYCNGGGGGGGGGGGGGGGGGG-OH
       |                |
       S                S
       |                |
       S                S
       |                |
 H-FVNQHLCGSHLVEALYLVCGERGFFYTPK-OH
```

MALDI-MS (matrix: sinapinic acid); m/z: 6765, Calculated: 6734.

Example 4

A22-45G desB30 Human Insulin

```
                    S————S
                    |    |
H-GIVEQCCTSICSLYQLENYCNGGGGGGGGGGGGGGGGGGGGGGGG-OH
       |                |
       S                S
       |                |
       S                S
       |                |
 H-FVNQHLCGSHLVEALYLVCGERGFFYTPK-OH
```

MALDI-MS (matrix: sinapinic acid); m/z: 7074, Calculated: 7075.

Example 5

A21Q A22-39[GPP]$_6$ desB30 Human Insulin

```
         S――――S
         |    |
H-GIVEQCCTSICSLYQLENYCQGPPGPPGPPGPPGPGPGPP-OH
     |        |
     S        S
     |        |
     S        S
     |        |
H-FVNQHLCGSHLVEALYLVCGERGFFYTPK-OH
```

MALDI-MS (matrix: sinapinic acid); m/z: 7228, Calculated: 7228.

Example 6

A21Q A22-39[GS]$_9$ desB30 Human Insulin

```
         S――――S
         |    |
H-GIVEQCCTSICSLYQLENYCQGSGSGSGSGSGSGSGS-OH
     |        |
     S        S
     |        |
     S        S
     |        |
H-FVNQHLCGSHLVEALYLVCGERGFFYTPK-OH
```

MALDI-MS (matrix: sinapinic acid); m/z: 7017, Calculated: 7017.

Example 7

A21Q A22-39[GE]$_9$ desB30 Human Insulin

```
         S――――S
         |    |
H-GIVEQCCTSICSLYQLENYCQGEGEGEGEGEGEGEGE-OH
     |        |
     S        S
     |        |
     S        S
     |        |
H-FVNQHLCGSHLVEALYLVCGERGFFYTPK-OH
```

MALDI-MS (matrix: sinapinic acid); m/z: 7394, Calculated: 7395.

Example 8

A21Q, A22-A45G, desB30 Human Insulin

```
         S――――S
         |    |
H-GIVEQCCTSICSLYQLENYCQGGGGGGGGGGGGGGGGGGGGGGGG-OH
     |        |
     S        S
     |        |
     S        S
     |        |
H-FVNQHLCGSHLVEALYLVCGERGFFYTPK-OH
```

MALDI-MS (matrix: sinapinic acid); m/z: 7060, Calculated: 7090.

Example 9

A21Q, A22-A51G, desB30 Human Insulin

```
         S――――S
         |    |
H-GIVEQCCTSICSLYQLENYCQGGGGGGGGGGGGGGGGGGGGGGGGGGGGGG-OH
     |        |
     S        S
     |        |
     S        S
     |        |
H-FVNQHLCGSHLVEALYLVCGERGFFYTPK-OH
```

MALDI-MS (matrix: sinapinic acid); m/z: 7433, Calculated: 7432.

Example 10

A21Q, A22-A57G, desB30 Human Insulin

MALDI-MS (matrix: sinapinic acid); m/z: 7774, Calculated: 7774.

Example 11

A21Q, A22-A45G, B(-6)-(-1G), desB30 Human Insulin

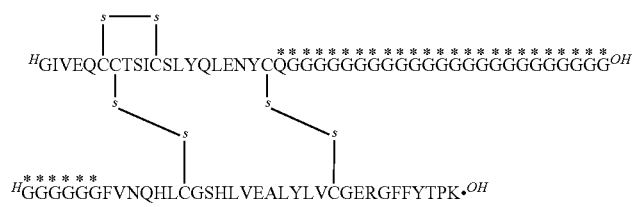

MALDI-MS (of single-chain precursor: B-chain N-terminal extension: EEAEAEAPK, C-peptide: DGK. Matrix: sinapinic acid); m/z: 8669, Calculated: 7432.

Example 12

A21Q, A22-A45G, B(-12)-(-1)G, desB30 Human Insulin

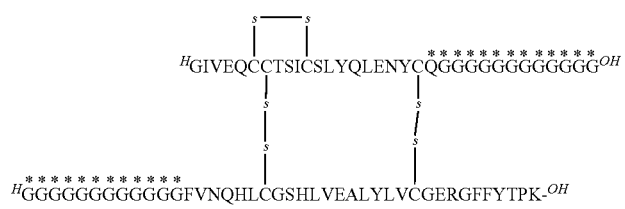

MALDI-MS (of single-chain precursor: B-chain N-terminal extension: EEAEAEAPK, C-peptide: DGK. Matrix: sinapinic acid); m/z: 9012, Calculated: 9011.

Example 13

A21Q, A22-A45G, B(-18)-(-1)G, desB30 Human Insulin

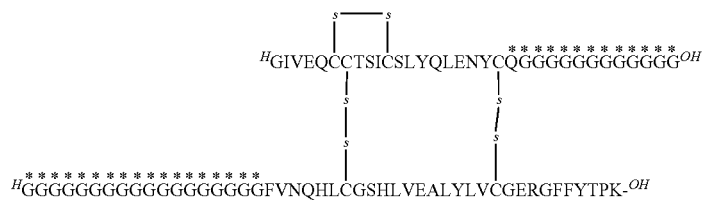

MALDI-MS (of single-chain precursor: B-chain N-terminal extension: EEAEAEAPK, C-peptide: DGK. Matrix: sinapinic acid); m/z: 9354, Calculated: 9353.

Example 14

A14E, A21Q, A22-A45G, B(-6)-(-1)G, B25H, desB30 Human Insulin

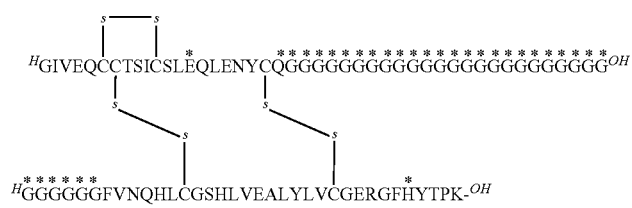

MALDI-MS (of single-chain precursor: B-chain N-terminal extension: EEAEAEAPK, C-peptide: DGK. Matrix: sinapinic acid); m/z: 8598, Calculated: 8596.

Example 15

A14E, A21Q, A22-A45G, B(-12)-(-1)G, B25H, desB30 Human Insulin

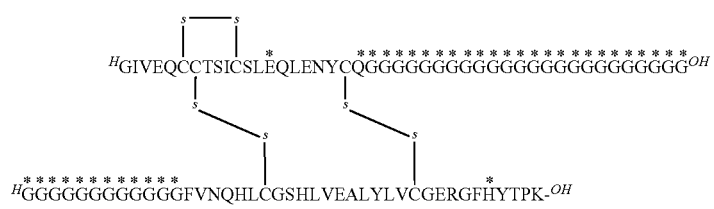

MALDI-MS (of single-chain precursor: B-chain N-terminal extension: EEAEAEAPK, C-peptide: DGK. Matrix: sinapinic acid); m/z: 8942, Calculated: 8937.

Example 16
A14E, A21Q, A22-A45G, B(-18)-(-1)G, B25H, desB30 Human Insulin
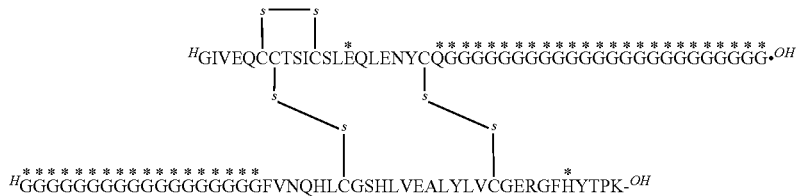
MALDI-MS (matrix: sinapinic acid); m/z: 8075, Calculated: 8073.
Example 17
A14E, A21Q, A22-A45G, B25H, desB30 Human Insulin
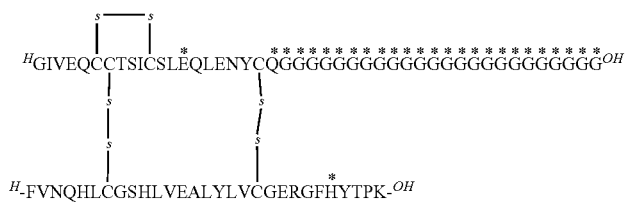
MALDI-MS (matrix: sinapinic acid); m/z: 7046, Calculated: 7046.
Example 18
A14E, A21Q, A22G-A51G, B25H, desB30 Human Insulin
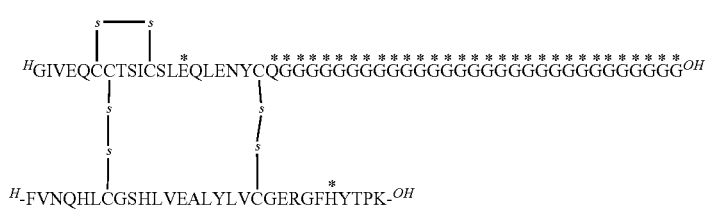
MALDI-MS (matrix: sinapinic acid); m/z: 7390, Calculated: 7388.

Example 19

A14E, A21Q, A22-A57G, B25H, desB30 Human Insulin

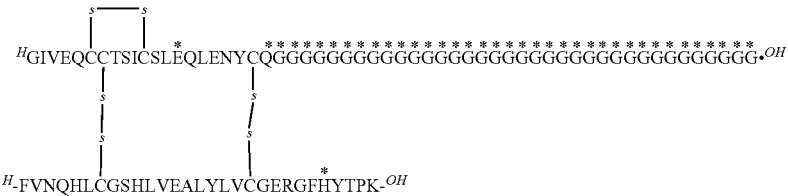

Example 20

A14E, A21Q, A22-A62G, B25H, desB30 Human Insulin

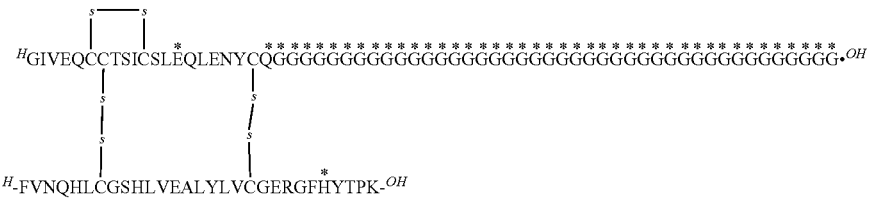

Other preferred insulins of the invention that may be prepared similarly include:
A21G A22-27G desB30 human insulin
A21G A22-33G desB30 human insulin
A21G A22-39G desB30 human insulin
A21G A22-45G desB30 human insulin
A21G A22-51G desB30 human insulin
A21G A22-57G desB30 human insulin
A21G A22-61G desB30 human insulin
A21Q A22-27G desB30 human insulin
A21Q A22-33G desB30 human insulin
A21Q A22-39G desB30 human insulin
A21Q A22-45G desB30 human insulin
A21 Q A22-51 G desB30 human insulin
A21Q A22-57G desB30 human insulin
A21Q A22-61G desB30 human insulin
A14E A21G A22-27G B25H desB30 human insulin
A14E A21G A22-33G B25H desB30 human insulin
A14E A21G A22-39G B25H desB30 human insulin
A14E A21G A22-45G B25H desB30 human insulin
A14E A21G A22-51G B25H desB30 human insulin
A14E A21G A22-57G B25H desB30 human insulin
A14E A21G A22-61G B25H desB30 human insulin
A14E A21Q A22-27G B25H desB30 human insulin
A14E A21Q A22-33G B25H desB30 human insulin
A14E A21Q A22-39G B25H desB30 human insulin
A14E A21Q A22-45G B25H desB30 human insulin
A14E A21Q A22-51G B25H desB30 human insulin
A14E A21Q A22-57G B25H desB30 human insulin
A14E A21Q A22-61G B25H desB30 human insulin
A21G A22-39[GPP]$_6$ desB30 human insulin
A14E, A21G A22-39[GPP]$_6$ B25H, desB30 human insulin
A21G A22-39[GPP]$_9$ desB30 human insulin
A14E, A21G A22-39[GPP]$_9$ B25H, desB30 human insulin
A21G A22-39[GS]$_9$ desB30 human insulin
A14E, A21G A22-39[GS]$_9$ B25H, desB30 human insulin
A21G A22-39[GE]$_9$ desB30 human insulin
A14E, A21G A22-39[GE]$_9$ B25H, desB30 human insulin
A14E, A21Q, A22-39[GPP]$_6$ B25H, desB30 human insulin A21Q, A22-39[GPP]$_9$ desB30 human insulin
A14E, A21Q A22-39[GPP]$_9$ B25H, desB30 human insulin
A21Q, A22-39[GS]$_9$ desB30 human insulin
A14E, A21Q, A22-39[GS]$_9$ B25H, desB30 human insulin
A21Q, A22-39[GE]$_9$ desB30 human insulin
A14E, A21Q, A22-39[GE]$_9$ B25H, desB30 human insulin

Example 21

The result of rat intratracheal drop instillation of the insulin of the above example 8 is given in FIG. 1.

Pharmacological Methods

Assay (I)

Insulin Receptor Binding of the Insulins of the Invention

The affinity of the insulins of the invention for the human insulin receptor can be determined by a SPA assay (Scintillation Proximity Assay) microtiterplate antibody capture assay. SPA-PVT antibody-binding beads, anti-mouse reagent (Amersham Biosciences, Cat No. PRNQ0017) are mixed with 25 ml of binding buffer (100 mM HEPES pH 7.8; 100 mM sodium chloride, 10 mM MgSO4, 0.025% Tween-20). Reagent mix for a single Packard Optiplate (Packard No. 6005190) is composed of 2.4 µl of a 1:5000 diluted purified recombinant human insulin receptor − (minus) exon 11, an amount of a stock solution of A14 Tyr[125I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl is then added and a dilution series is made from appropriate samples. To the dilution series is then added 100 µl of reagent mix and the samples are incubated for 16 hours while gently shaken. The phases are then separated by centrifugation for 1 min and the plates counted in a Top-counter. The binding data are fitted using the nonlinear regression algorithm in the GraphPad Prism 2.01 (GraphPad Software, San Diego, Calif.).

| Example # | Relative insulin receptor binding |
|---|---|
| 1 | 44% |
| 2 | 41% |
| 3 | 30% |
| 4 | 25% |
| 8 | 14% |
| 9 | 17% |
| 10 | 20% |
| 11 | 14% |
| 12 | 16% |
| 13 | 13% |
| 14 | 10% |
| 15 | 11% |
| 16 | 7.2% |
| 17 | 12% |
| 18 | 12% |
| 19 | 14% |
| 20 | 2% |

Assay (II)

Potency of the Insulins of the Invention Relative to Human Insulin

Wistar rats are used for testing the blood glucose lowering efficacy of the insulins of the invention after i.v. bolus administration. Following administration the of either insulin of the invention or human insulin the concentration of blood glucose is monitored Assay (III)

Determination in Pigs of T50% of the Insulins of the Invention

T50% is the time when 50% of an injected amount of the A14 Tyr[125I] labelled derivative of an insulin to be tested has disappeared from the injection site as measured with an external γ-counter.

The principles of laboratory animal care are followed, Specific pathogen-free LYYD, non-diabetic female pigs, crossbreed of Danish Landrace, Yorkshire and Duroc, are used (Holmenlund, Haarloev, Denmark) for pharmacokinetic and pharmacodynamic studies. The pigs are conscious, 4-5 months of age and weighing 70-95 kg. The animals are fasted overnight for 18 h before the experiment.

Formulated preparations of extended insulins labelled in TyrA14 with 125I are injected sc. in pigs as previously described (Ribel, U., Jørgensen, K, Brange, J, and Henriksen, U. The pig as a model for subcutaneous insulin absorption in man. Serrano-Rios, M and Lefèbvre, P. J. 891-896. 1985. Amsterdam; New York; Oxford, Elsevier Science Publishers. 1985 (Conference Proceeding)).

At the beginning of the experiments a dose of 60 nmol of the extended insulin according to the invention (test compound) and a dose of 60 nmol of insulin (both 125I labelled in TyrA14) are injected at two separate sites in the neck of each pig.

The disappearance of the radioactive label from the site of sc. injection is monitored using a modification of the traditional external gamma-counting method (Ribel, U. Subcutaneous absorption of insulin analogues. Berger, M. and Gries, F. A. 70-77 (1993). Stuttgart; New York, Georg Thime Verlag (Conference Proceeding)). With this modified method it is possible to measure continuously the disappearance of radioactivity from a subcutaneous depot for several days using cordless portable device (Scancys Laboratorieteknik, Værløse, DK-3500, Denmark). The measurements are performed at 1-min intervals, and the counted values are corrected for background activity.

Assay (IV)

Pulmonary Delivery of Extended Insulins to Rats

The test substance will be dosed pulmonary by the drop instillation method. In brief, male Wistar rats (app. 250 g) are anaesthesized in app. 60 ml fentanyl/dehydrodenzperidol/-dormicum given as a 6.6 ml/kg sc primingdose and followed by 3 maintenance doses of 3.3 ml/kg sc with an interval of 30 min. Ten minutes after the induction of anaesthesia, basal samples are obtained from the tail vein (t=−20 min) followed by a basal sample immediately prior to the dosing of test substance (t=0). At t=0, the test substance is dosed intra tracheally into one lung. A special cannula with rounded ending is mounted on a syringe containing the 200 ul air and test substance (1 ml/kg). Via the orifice, the cannula is introduced into the trachea and is forwarded into one of the main bronchi—just passing the bifurcature. During the insertion, the neck is palpated from the exterior to assure intratracheal positioning. The content of the syringe is injected followed by 2 sec pause. Thereafter, the cannula is slowly drawn back. The rats are kept anaesthesized during the test (blood samples for up to 4 hrs) and are euthanized after the experiment.

Assay (V)

Hydrophobicity of Extended Insulins According to the Invention

The hydrophobicity (hydrophobic index) of extended insulins of the invention relative to human insulin, $k'_{rel}$, was measured on a LiChrosorb RP18 (5 µm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{human}$, was adjusted to at least $2t_0$ by varying the ratio between the A and B solutions. $k'_{rel}=(t_{insulin}-t_0)/(t_{human}-t_0)$.

What is claimed is:

1. An amino acid extended human insulin, said extended insulin comprising an insulin in which an amino acid oligomer is attached to the C-terminal end of the A chain of said insulin and/or to the N-terminal end of the B chain of said insulin, wherein each amino acid oligomer is selected from the group consisting of $(Gly)_n$, $(Gly-Pro-Pro)_n$, $(Pro-Pro-Gly)_n$, $(Gly-Ser)_n$, $(Ser-Gly)_n$, $(Gly-Glu)_n$ or $(Glu-Gly)_n$, wherein n is an integer resulting in 5 to 50 amino acid residues per oligomer;
wherein said insulin has one or more of the following modifications:
in the A14 position: E or D;
in the A21 position: G, A or Q;
in the B3 position: Q, S or T;
in the B25 position: H;
in the B28 position: D or E;
in the B30 position: des; and wherein said extended insulin exhibits a prolonged action profile following administration.

2. The extended insulin of claim 1, wherein the amount of Gly residues in each amino acid oligomer is at least 80% (weight/weight).

3. The extended insulin of claim 2, wherein each amino acid oligomer is composed of Gly residues.

4. The extended insulin of claim 1, wherein the amino acid oligomer is attached to an amino acid residue in one of the B1 or A21 of insulin, provided said amino acid is in the N-terminal position of the B chain of said insulin or in the C-terminal position of the A chain of said insulin respectively prior to attachment of the oligomer.

5. The extended insulin of claim 1, wherein an amino acid oligomer is separately attached by a peptide bond to each of the C-terminal end of the A chain of said insulin and to the N-terminal end of the B chain of said.

6. The extended insulin of claim 1, wherein an amino acid oligomer is attached by a peptide bond to either the C-terminal end of the A chain of said insulin or to the N-terminal end of the B chain of said insulin.

7. The extended insulin of claim 1, wherein the amino acid oligomer is attached to an amino acid residue in one of the positions B1 or A21 of insulin, provided said amino acid is in the N-terminal position of the B chain of said insulin or in the C-terminal position of the A chain of said insulin respectively prior to attachment of the oligomer.

8. The extended insulin of claim 7, wherein an amino acid oligomer is separately attached by a peptide bond to each of the C-terminal end of the A chain of said insulin and the N-terminal end of the B chain of said insulin.

9. The extended insulin of claim 7, wherein an amino acid oligomer is attached by a peptide bond to either the C-terminal end of the A chain of said insulin or to the N-terminal end of the B chain of said insulin.

10. The extended insulin of claim 1, wherein an amino acid oligomer is attached by a peptide bond to each of the C-terminal end of the A chain of said insulin and the N-terminal end of the B chain of said insulin.

11. The extended insulin of claim 1, wherein said extended insulin comprising an insulin in which an amino acid oligomer containing between 5 and 50 amino acids is attached to the C-terminal end of the A chain of said insulin.

12. The extended insulin of claim 11, wherein the amino acid oligomer is composed of amino acid residues selected from the group consisting of Gly, Glu, Pro and Ser residues.

13. The extended insulin of claim 12, wherein the amount of Gly residues in the amino acid oligomer is at least 80% (weight/weight).

14. The extended insulin of claim 13, wherein the amino acid oligomer is composed of Gly residues.

15. The extended insulin of claim 12, wherein the amino acid oligomer is selected from the group consisting of $(Gly)_n$, $(Gly\text{-}Pro\text{-}Pro)_n$, $(Pro\text{-}Pro\text{-}Gly)_n$, $(Gly\text{-}Ser)_n$, $(Ser\text{-}Gly)_n$, $(Gly\text{-}Glu)_n$ or $(Glu\text{-}Gly)_n$, wherein n is an integer giving a number of amino acid residues per oligomer between 5 and 50.

* * * * *

SEQUENCE LISTING

<160> NUMBER OF SEQ ID NOS: 8

<210> SEQ ID NO 1
<211> LENGTH: 27
<212> TYPE: PRT
<213> ORGANISM: Artificial
<220> FEATURE:
<223> OTHER INFORMATION: Synthetic

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn Gly Gly Gly Gly Gly Gly

```
                  20                  25

<210> SEQ ID NO 2
<211> LENGTH: 29
<212> TYPE: PRT
<213> ORGANISM: Artificial
<220> FEATURE:
<223> OTHER INFORMATION: Synthetic

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 3
<211> LENGTH: 33
<212> TYPE: PRT
<213> ORGANISM: Artificial
<220> FEATURE:
<223> OTHER INFORMATION: Synthetic

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn Gly Gly Gly Gly Gly Gly Gly Gly Gly
            20                  25                  30

Gly

<210> SEQ ID NO 4
<211> LENGTH: 39
<212> TYPE: PRT
<213> ORGANISM: Artificial
<220> FEATURE:
<223> OTHER INFORMATION: Synthetic

<400> SEQUENCE: 4

Gly Ile Val Glu Gln Cys Cys Thr Ser Ile Cys Ser Leu Tyr Gln Leu
1               5                   10                  15

Glu Asn Tyr Cys Asn Gly Gly Gly Gly Gly Gly Gly Gly Gly
            20                  25                  30

Gly Gly Gly Gly Gly Gly Gly
        35

<210> SEQ ID NO 5
<211> LENGTH: 45
<212> TYPE: PRT
<213> ORGANISM: Artificial
<220> FEATURE:
<223> OTHER INFORMATION: Synthetic

<400> SEQUENCE: 5

Gly Ile Val Glu Gln Cys Cys Thr Ser Ile Cys Ser Leu Tyr Gln Leu
1               5                   10                  15

Glu Asn Tyr Cys Asn Gly Gly Gly Gly Gly Gly Gly Gly Gly
            20                  25                  30

Gly Gly Gly Gly Gly Gly Gly Gly Gly Gly Gly Gly
            35                  40                  45

<210> SEQ ID NO 6
<211> LENGTH: 39
<212> TYPE: PRT
<213> ORGANISM: Artificial
```

```
<220> FEATURE:
<223> OTHER INFORMATION: Synthetic

<400> SEQUENCE: 6

Gly Ile Val Glu Gln Cys Cys Thr Ser Ile Cys Ser Leu Tyr Gln Leu
1               5                   10                  15

Glu Asn Tyr Cys Gln Gly Pro Pro Gly Pro Pro Gly Pro Pro Gly Pro
            20                  25                  30

Pro Gly Pro Pro Gly Pro Pro
        35

<210> SEQ ID NO 7
<211> LENGTH: 39
<212> TYPE: PRT
<213> ORGANISM: Artificial
<220> FEATURE:
<223> OTHER INFORMATION: Synthetic

<400> SEQUENCE: 7

Gly Ile Val Glu Gln Cys Cys Thr Ser Ile Cys Ser Leu Tyr Gln Leu
1               5                   10                  15

Glu Asn Tyr Cys Gln Gly Ser Gly Ser Gly Ser Gly Ser Gly Ser Gly
            20                  25                  30

Ser Gly Ser Gly Ser Gly Ser
        35

<210> SEQ ID NO 8
<211> LENGTH: 39
<212> TYPE: PRT
<213> ORGANISM: Artificial
<220> FEATURE:
<223> OTHER INFORMATION: Synthetic

<400> SEQUENCE: 8

Gly Ile Val Glu Gln Cys Cys Thr Ser Ile Cys Ser Leu Tyr Gln Leu
1               5                   10                  15

Glu Asn Tyr Cys Gln Gly Glu Gly Glu Gly Glu Gly Glu Gly Glu Gly
            20                  25                  30

Glu Gly Glu Gly Glu Gly Glu
        35
```